United States Patent [19]

Nicholson et al.

[11] Patent Number: 4,899,743
[45] Date of Patent: Feb. 13, 1990

[54] SUTURE ANCHOR INSTALLATION TOOL

[75] Inventors: James E. Nicholson, Lincoln; Roland F. Gatturna, Walpole, both of Mass.

[73] Assignee: Mitek Surgical Products, Inc., Norwood, Mass.

[21] Appl. No.: 132,940

[22] Filed: Dec. 15, 1987

[51] Int. Cl.$^4$ ............... A61B 17/04; A61B 17/08; A61F 5/04

[52] U.S. Cl. .................................. 606/139; 606/72

[58] Field of Search ............... 128/337, 330, 334 R, 128/92 YC, 92 YF, 92 VD, 335

[56] References Cited

U.S. PATENT DOCUMENTS

| | | | |
|---|---|---|---|
| 3,716,058 | 2/1973 | Tanner, Jr. | 128/335 |
| 4,007,732 | 2/1972 | Kvavle et al. | 128/754 |
| 4,124,026 | 11/1978 | Berner et al. | 128/303 R |
| 4,657,461 | 4/1987 | Smith | 411/340 |
| 4,665,906 | 5/1987 | Jervis | 128/92 YN |
| 4,669,473 | 6/1987 | Richards et al. | 128/334 C |
| 4,741,330 | 5/1988 | Hayhurst | 128/92 YF |

Primary Examiner—Edward M. Coven
Assistant Examiner—Gary Jackson
Attorney, Agent, or Firm—Schiller, Pandiscio and Kusmer

[57] ABSTRACT

A novel suture anchor installation tool which comprises an elongated member having a first end and a second end and a slot extending from the first end towards the second end, the slot being sized to snugly accommodate the suture anchor's barb, whereby the suture anchor may be attached to the elongated member at the first end of the elongated member by fitting the barb into the slot so that the barb extends upward and outward from the first end of the elongated member, through the slot, with the body of the suture anchor engaging the first end of the installation tool.

In use, the suture is first attached to the suture anchor and then the suture anchor is attached to the elongated member in the foregoing manner. Then the first end of the elongated member is pressed into a predrilled hole in the bone, forcing the suture anchor in ahead of it. As the suture anchor is pressed into the bone, its barb engages the side wall of the bone and is forced to retract backwards into the elongated member's slot so that it extends somewhat parallel to the elongated member. When the suture anchor bottoms out in the bone hole, and the elongated member is thereafter withdrawn, the barb's engagement with the bone wall will cause the suture anchor to separate from the elongated member, leaving the suture anchor (and its attached suture) anchored securely in the bone.

28 Claims, 7 Drawing Sheets

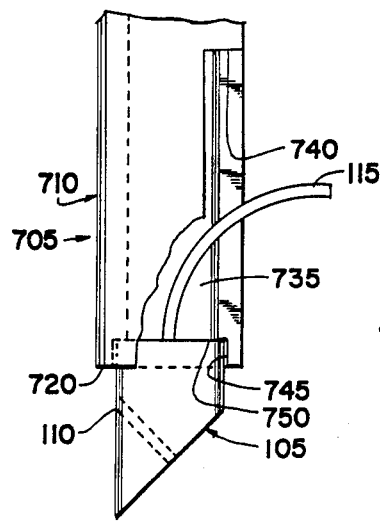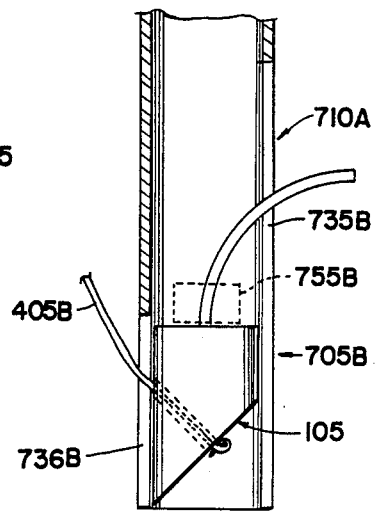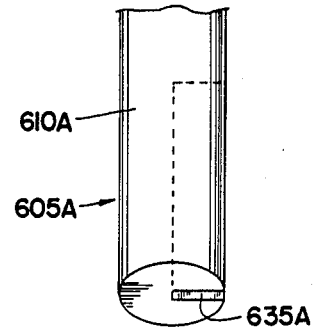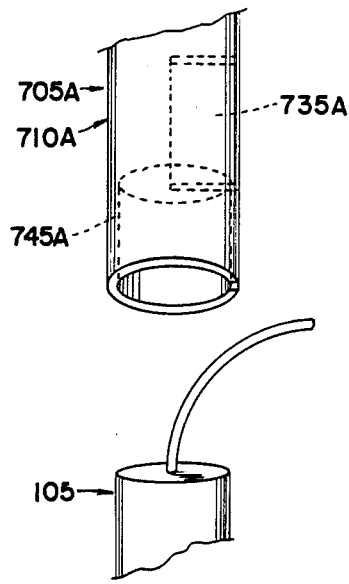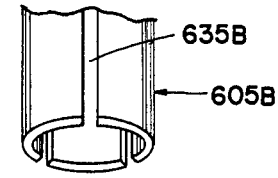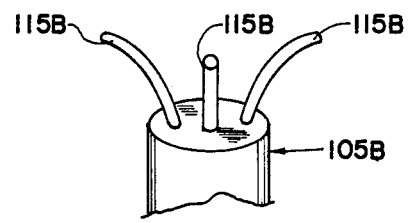

SUTURE ANCHOR INSTALLATION TOOL

FIELD OF THE INVENTION

This invention relates to surgical devices in general, and more particularly to installation tools for deploying suture anchors of the sort adapted to anchor one end of a piece of conventional suture in bone.

BACKGROUND OF THE INVENTION

In copending U.S. patent application Ser. No. 051,367, filed 5/18/87 by Roland F. Gatturna et al. for "Suture Anchor", there is disclosed a variety of suture anchors of the sort adapted to anchor one end of a piece of conventional suture in bone, and there is disclosed several suture anchor installation tools for deploying such suture anchors in bone.

The specification and drawings of the above-identified U.S. patent application Ser. No. 051,367 is hereby incorporated by reference into the present patent application.

Looking now at FIG. 1, there is shown one of the suture anchors disclosed in the above-identified U.S. patent application Ser. No. 051,367. This suture anchor, identified generally by the numeral 105, comprises a coupling member 110 and a barb 115.

Coupling member 110 comprises a piece of 6A14V titanium alloy having a first end surface 120 and a second end surface 125. First end surface 120 is disposed at an angle of approximately 30 degrees to the coupling member's longitudinal axis, and second end surface 125 is disposed at a right angle to the coupling member's longitudinal axis, as shown. Coupling member 110 has a blind hole 130 opening on second end surface 125, and a bore 135 extending at an angle between the coupling member's side wall and its bottom end surface 120, as shown. Bore 135 extends at a right angle to the coupling member's bottom end surface 120. In the case of a suture anchor adapted to anchor a No. 0 suture (i.e., a suture having a diameter of approximately 0.014 inch), coupling member 110 preferably has a length of approximately 0.160 inch and a diameter of approximately 0.053 inch, blind hole 130 has a depth of approximately 0.070 inch and a diameter of approximately 0.028 inch, and bore 135 has a diameter of approximately 0.028 inch.

Barb 115 comprises a curved length of nickel titanium alloy having a first end 140 and a second end 145. In the case of a suture anchor adapted to anchor a No. 0 suture, barb 115 preferably has a diameter of approximately 0.026 inch and, in its unrestrained state, comprises an arc of approximately 135 degrees of a loop approximately 0.250 inch in diameter (when measured to the inside of the loop). Barb 115 is attached to the coupling member by fitting the barb's first end 140 into the coupling member's blind hole 130, whereby the barb's second end 145 extends upward and outward from the coupling member. Coupling member 110 is then crimped inward at one or more points as shown at 150 to lock barb 115 to the coupling member. Barb 115 is made of such a nickel titanium alloy that it is capable of being elastically deformed to a substantially straight length when desired (i.e., so that the barb's second end 145 is aligned with its first end 140, as well as with the opposite ends of the coupling member). By way of example, barb 115 may be made out of binary nitinol such as that sold by Furukawa of Japan and Raychem Corporation of Menlo Park, Calif., or it might be made out of ternary nitinol such as that sold by Raychem Corporation and described in U.S. Pat. No. 4,505,767 (Quinn).

Looking next at FIG. 2, there is shown one of the suture anchor installation tools disclosed in the above-identified U.S. patent application Ser. No. 051,367. This suture anchor installation tool, identified generally by the numeral 205, may be used to deploy the suture anchor shown in FIG. 1. Installation tool 205 comprises a hollow sheath or cannula 210, a hollow loader or inserter 215 and a solid (or hollow) plunger 220.

Hollow sheath 210 terminates in a flat annular surface 225 at its front end and a flat annular surface 230 at its rear end. Surfaces 225 and 230 are disposed at an angle substantially perpendicular to the longitudinal axis of sheath 210. Sheath 210 has an axial bore 235 extending between its front and rear surfaces 225 and 230. Sheath 210 includes a disk-like finger grip 240 which is affixed to the rear end of the outer sheath member and includes a flat surface 245 which is coplanar with the sheath member's rear surface 230. In the case of an installation tool adapted to deploy a suture anchor for anchoring a No. 0 suture, sheath 210 preferably has an outer diameter (i.e., forward of finger grip 240) of approximately 0.083 inch, an inner diameter of approximately 0.071 inch, and a length of approximately 4.0 inches.

Hollow loader 215 terminates in a flat annular surface 250 at its front end and a flat annular surface 255 at its rear end. Surfaces 250 and 255 are disposed at an angle substantially perpendicular to the longitudinal axis of loader 215. Loader 215 has an axial bore 260 extending between its front surface 250 and its rear surface 255. Loader 215 includes a disk-like finger grip 265 which is attached to the rear end of the loader member and includes a flat surface 270 that is coplanar with the loader's rear surface 255. Loader 215 is sized so that it will make a close sliding fit within bore 235 of sheath 210, as will hereinafter be described in further detail, and also so that its leading tip 250 will not protrude from the front end of sheath member 210 when the loader is inserted into the sheath's axial bore 235 and the loader's finger grip 265 is in engagement with the sheath's rear surface 230, as will hereinafter be described in further detail. In the case of an installation tool adapted to deploy a suture anchor for anchoring a No. 0 suture, loader 215 preferably has an outer diameter (i.e., forward of finger grip 265) of approximately 0.065 inch, an inner diameter of approximately 0.047 inch, and a length of approximately 4.13 inches.

Plunger 220 includes a solid (or hollow) body section 275 and a head section 280. Body section 275 has a round cross-section and terminates in a front surface 285. Plunger 220 is sized so that its body section 275 will make a close sliding fit within bore 260 of loader 215 and also so that its leading tip 285 will protrude from the front end of the loader member a short distance when the plunger's head section 280 is in engagement with the loader member's rear surface 270, as will hereinafter be described in further detail. In the case of an installation tool adapted to deploy a suture anchor for anchoring a No. 0 suture, plunger 220 preferably has a diameter of approximately 0.047 inch forward of head section 280, and a length of approximately 4.32 inches, as will hereinafter be described in further detail.

Installation tool 205 is intended to be utilized as follows. Looking next at FIG. 3, suture anchor 105 is loaded into the top end of sheath member 210 so that the suture anchor's coupling member 110 resides inside the sheath's axial bore 235 and the suture anchor's barb 115 extends above finger grip 240 of the sheath member. Looking next at FIG. 4, the front end 250 of loader 215 is then slipped over the free end of the suture anchor's barb 115 so that the free end of the barb extends into the loader member's axial bore 260. Then loader member 215 is (a) forced into coaxial alignment with outer sheath member 210, thereby straightening out barb 115 in the process, and (b) pushed into the interior of sheath member 210, carrying the suture anchor downward within the sheath member as it goes. In order to assure that barb 115 of suture anchor 105 is contained completely within loader 215 such that suture anchor loader surface 250 contacts suture anchor surface 125, the sheath's bottom surface 225 is rested against a stationary surface 305 (see FIG. 5) while suture anchor loader 215 is brought downward into direct contact with the suture anchor's rear surface 125. Sheath member 210 and loader member 215 are carefully sized relative to one another (and relative to suture anchor 105) so that when the loader member's finger grip 265 is thereafter brought into contact with the sheath member's top surface 245, the suture anchor will protrude slightly from the bottom end of the sheath member, as shown in FIG. 6. More specifically, as seen in FIGS. 7 and 8, sheath member 210 and loader member 215 are sized relative to one another (and relative to suture anchor 105) so that both ends of the suture anchor's diagonal bore 135 will be exposed to view when the loader member's finger grip 265 is brought into contact with the sheath member's top surface 245. With the suture anchor so held by the installation tool, a conventional suture 405 may then be easily attached to the suture anchor by passing the suture through the anchor's diagonal bore 135 and tying a knot 410 at the end of the suture which can then bear against the bottom end 120 of the suture anchor's coupling member, as shown in FIGS. 7 and 8.

Once the suture has been attached to the suture anchor in the foregoing manner, plunger member 220 may then be inserted into the loader member's internal bore 260 (see FIG. 9) and pressed downward until its bottom tip 285 contacts the suture anchor barb contained in the loader member's bore 260. By appropriately sizing the respective members involved, the head section 280 of the plunger member will remain slightly above finger grip 265 of loader member 215 when the plunger member's tip 285 engages barb 115 of suture anchor 105.

Thereafter, when the installation tool is actuated to deploy the suture anchor (and its attached suture) into bone, the tip of the installation tool is inserted into a hole 505 formed in a bone 510 until the suture anchor rests on the bone surface 515 (see FIG. 10), and then head section 280 of plunger member 220 is held stationary while finger grip 240 of sheath member 210 is pulled upward so that the loader's flat surface 270 engages the underside of the plunger's head section 280, thereby ejecting the suture anchor 105 (and its attached suture 405) out of the installation tool and into the bone, as shown in FIGS. 10 and 11.

Complete details regarding the construction and use of suture anchor 105 and installation tool 205 are provided in the above-identified U.S. patent application Ser. No. 051,367, which is incorporated herein by reference; the foregoing description is provided merely for convenient reference in understanding the present invention.

With the three-element installation tool 205 described above, a hole slightly larger in size than the combined diameters of the outer sheath member 210 and the suture 405 must be drilled in the bone. For example, with a suture anchor for anchoring a No. 0 suture, where the suture anchor's coupling member 110 has a diameter of approximately 0.053 inch, suture 405 has a diameter of approximately 0.014 inch, and outer sheath 210 has a diameter of approximately 0.083 inch, a hole approximately 0.098 inch in diameter must be drilled in the bone. In the case of a suture anchor for anchoring a No. 2 suture, where the suture anchor's coupling member 110 has a diameter of approximately 0.061 inch, suture 405 has a diameter of approximately 0.020 inch, and outer sheath 210 has a diameter of approximately 0.095 inch, a hole approximately 0.116 inch in diameter must be drilled in the bone.

A summary table of such sizing is given below:

TABLE 1

|  | Suture Size: | |
| --- | --- | --- |
|  | No. 0 | No. 2 |
| Suture Anchor Dia. | 0.053 | 0.061 |
| Sheath Diameter | 0.083 | 0.095 |
| Suture Diameter | 0.014 | 0.020 |
|  | — | — |
| Sheath + Suture Dia. | 0.097 | 0.115 |
| Drill Diameter | 0.098 | 0.116 |
| (Drill hole) − (Suture Anchor) | 0.045 | 0.055 |

Unfortunately, while the three-element installation tool 205 described above is known to work, it is also believed to suffer from a number of disadvantages.

For one thing, it will be seen from Table 1 above that the three-element installation tool 205 takes up a substantial amount of room in the bone hole relative to the diameter of the suture anchor. More specifically, as seen in Table 1 above, the suture anchor for anchoring a No. 0 suture has a coupling member diameter of approximately 0.053 inch, yet it requires a drilled hole of approximately 0.098 inch to accommodate the suture anchor when it is set by installation tool 205. Therefore, the suture anchor's barb must essentially take up the difference between the 0.053 inch coupling member and the 0.098 inch hole when the suture anchor is set in the hole. Thus, the barb must expand approximately 0.045 inch for the suture anchor used to anchor a No. 0 suture. Similarly, as seen in Table 1 above, the suture anchor for anchoring a No. 2 suture has a coupling member diameter of approximately 0.061 inch, yet it requires a drilled hole of approximately 0.116 inch to accommodate the suture anchor when it is set by installation tool 205. Therefore, the barb must essentially take up the difference between the 0.061 inch coupling member and the 0.116 inch hole when the suture anchor is set in the hole. Thus, the barb must expand approximately 0.055 inch for the suture anchor used to anchor a No. 2 suture. Inasmuch as the barb loses force as it returns closer and closer to its original curved shape from its constrained straight shape (e.g. much like a spring), the larger the difference existing between the bone hole diameter and the suture anchor body, the smaller the force applied to the side wall of the bone by the suture anchor's barb when the suture anchor is set in the bone, and hence the weaker the attachment of the suture anchor to the bone. Accordingly, a fit such as that mandated by the use of the three-element installation tool 205 could possibly lead to inconsistent anchoring of the suture in the bone.

Another disadvantage of the three-element installation tool 205 described above is that the outer sheath 210 and loader member 215 can be preloaded with the suture anchor (in the manner shown in FIGS. 5 and 6) but, if it is then left for a substantial amount of time between loading and use, the barb can lose its resiliency and relax over time, so that when the suture anchor is thereafter used, its barb may not contact the bone wall with the same force that it would have if the suture anchor had been used immediately after loading the suture anchor into sheath 210 and loader 215. Accordingly, preloading accompanied by delayed use can possibly lead to inconsistent and unsatisfactory anchoring of the bone anchor in the bone.

OBJECTS OF THE INVENTION

Accordingly, the principal object of the present invention is to provide a novel suture anchor installation tool which improves upon the three-element installation tool of the above-identified U.S. patent application Ser. No. 051,367.

Another object of the present invention is to provide a suture anchor installation tool which minimizes the gap between the body of the suture anchor and the bone hole, whereby less expansion of the barb will be required to fix the suture anchor in the bone and a tighter attachment of the suture anchor to the bone will result.

Still another object of the present invention is to provide a suture anchor installation tool in which the suture anchor's barb is not deformed to a straight length when it is loaded into the installation tool, whereby the holding power of the suture anchor will not deteriorate when the suture anchor is stored for a long period of time in the installation tool prior to use.

And still another object of the present invention is to provide a novel method for deploying a suture anchor in bone.

SUMMARY OF THE INVENTION

These and other objects of the present invention are achieved through the use of a novel suture anchor installation tool which comprises an elongated member having a first end and a second end and a slot extending from the first end towards the second end, the slot being sized to snugly accommodate the suture anchor's barb therein, whereby the suture anchor may be attached to the elongated member at the first end of the elongated member by fitting the barb into the slot so that the barb extends upward and outward from the first end of the elongated member, through the slot, with the flat end of the suture anchor's coupling member engaging the first end of the installation tool.

In use, the suture is first attached to the suture anchor, and then the suture anchor is attached to the installation tool in the foregoing manner. Then the first end of the elongated member is inserted into the pre-drilled hole in the bone, forcing the suture anchor in ahead of it. As the suture anchor is pressed into the bone, its barb engages the side wall of the bone and is forced to retract backwards into the elongated member's slot, so that the barb extends somewhat parallel to the elongated member. When the suture anchor bottoms out in the bone hole, the elongated member is then withdrawn, whereupon the barb's engagement with the bone wall causes the suture anchor to separate from the elongated member, leaving the suture anchor (and its attached suture) anchored securely in the bone.

BRIEF DESCRIPTION OF THE DRAWINGS

Still other objects and features of the present invention will be more fully described or rendered obvious in the following detailed description of the invention, which is to be considered together with the accompanying drawings wherein like numbers refer to like parts and further wherein:

FIG. 19 is a partial perspective view showing a second embodiment of the suture anchor installation tool;

FIG. 20 is a partial side elevation showing a third embodiment of the suture anchor installation tool receiving a suture anchor;

FIG. 21A is a partial perspective view showing a fourth embodiment of the suture anchor installation tool;

FIG. 21B is a partial side elevation showing a fifth embodiment of the suture anchor installation tool;

FIG. 22 is a partial perspective view showing a sixth embodiment of the suture anchor installation tool;

DETAILED DESCRIPTION OF THE INVENTION

Figures 12, 13:
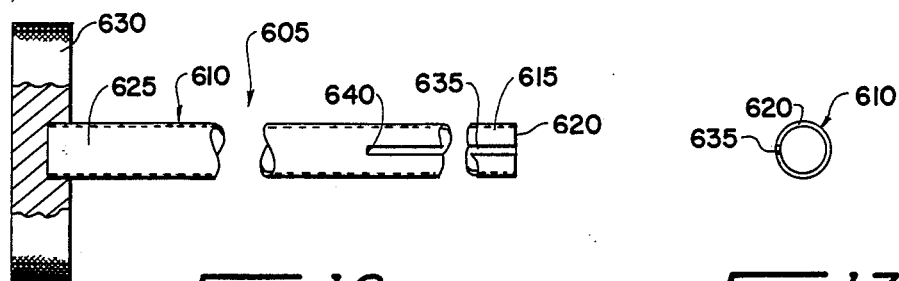
FIG. 12 is a side view in elevation, partly in section, showing the preferred embodiment of the suture anchor installation tool which constitutes the present invention.
FIG. 13 is an end view in elevation showing the distal end of the suture anchor installation tool of FIG. 12.

Looking now at FIGS. 12 and 13, there is shown a suture anchor installation tool 605 which constitutes the preferred embodiment of the present invention. Installation tool 605 comprises a hollow cannula 610 having a distal end 615 terminating in a flat end surface 620 and a rear end 625 terminating in a flat disk or knob 630. A longitudinally-extending slot 635 is formed in the side wall of cannula 610. Slot 635 begins at the cannula's distal end surface 620 and terminates in a rear surface 640.

Installation tool 605 is adapted to be used to install a suture anchor such as the suture anchor 105 previously described, and to this end it is important that installation tool 605 be dimensioned in accordance with the dimensions of the actual suture anchor being deployed by the tool. Specifically, it is important that suture anchor installation tool 605 be sized so that (a) its cannula 610 has an outer diameter smaller than, equal to or just slightly larger than the outer diameter of the suture anchor's coupling member 110 so that the smallest possible hole may be formed in the bone which is to receive the bone anchor, (b) its cannula 610 has an internal diameter smaller than the outer diameter of the suture anchor's coupling member 110, so that the coupling member will not be able to slip inside the cannula, (c) its slot 635 has a width equal to or just slightly larger than the diameter of the suture anchor's barb 115, so that the barb will fit snugly between the walls of cannula 610 which define its slot 635, as will hereinafter be described in further detail, and (d) its slot 635 has a length sufficient to accommodate the suture anchor's barb 115 when the barb is bent backwards into the cannula during deployment of the suture anchor, as will hereinafter be described in further detail.

For example, in the case where suture anchor 105 is to be used to anchor a No. 0 suture, so that the suture anchor has the dimensions identified above, cannula 610 preferably has an inner diameter of approximately 0.050 inch and an outer diameter of approximately 0.058 inch, slot 635 has a length (i.e., when measured from flat end surface 620 to slot rear surface 640) of approximately 0.370 inch and a width of approximately 0.031 inch. In the case where suture anchor 105 is to be used to anchor a No. 2 suture, the same installation tool may be used, since the suture anchor used in conjunction with a No. 2 suture will have the same size barb and an even wider diameter coupling member than the suture anchor used in conjunction with a No. 0 suture. Preferably, suture anchor installation tool 605 has an overall length, when measured from distal end 620 to the rear of disk 630, of approximately 4.0 inches.

In use, a suture is first attached to suture anchor 105, then the suture anchor is attached to the distal end of installation tool 605, and then the suture anchor is deployed into a hole formed in the bone using installation tool 605.

Figure 14A:
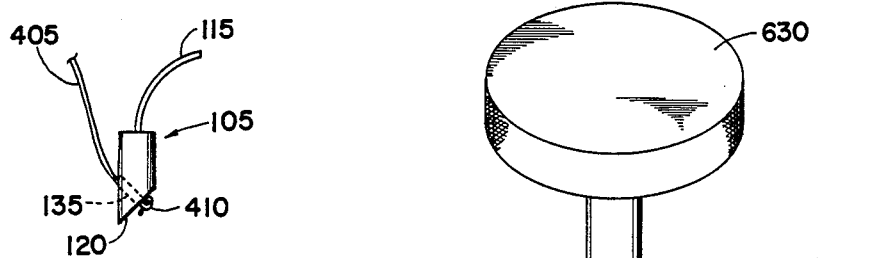
FIG. 14A is a side view in elevation showing the suture being attached to the suture anchor remote from the installation tool.
Figure 14B:
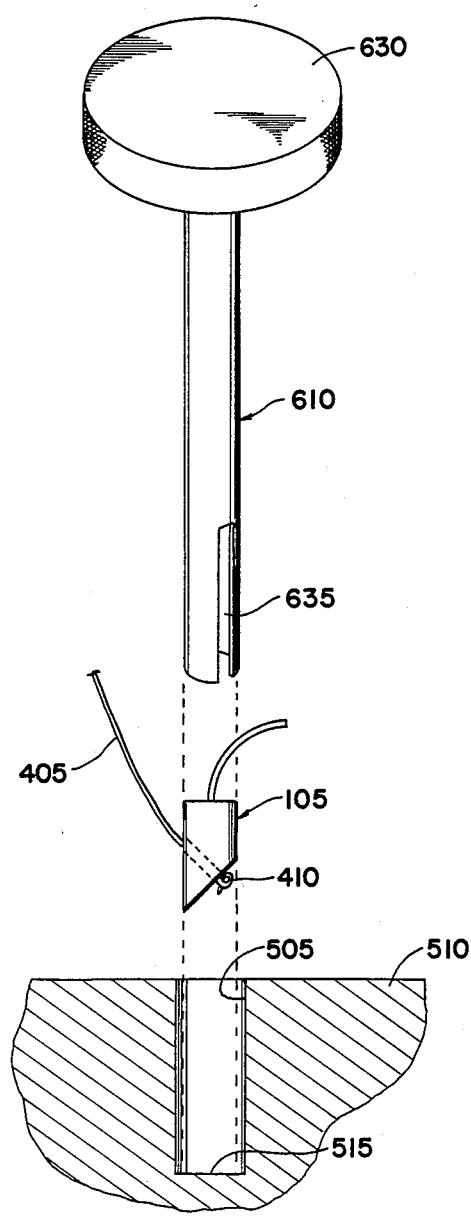
FIG. 14B is a perspective view showing the suture and suture anchor of FIG. 14A, the installation tool of FIGS. 12 and 13, and a target bone which is to receive the suture anchor, all in exploded relation to one another.
Figure 15:
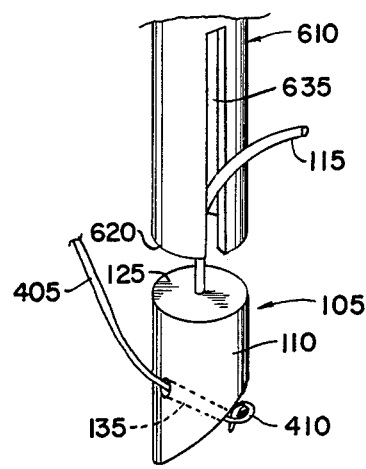
FIG. 15 is an enlarged partial perspective view showing the suture anchor of FIG. 1 being loaded onto the distal end of the suture anchor installation tool of FIGS. 12 and 13.

More specifically, and looking now at FIGS. 14A, 14B and 15, the suture is first attached to the suture anchor in the manner shown in FIG. 14A, i.e., by passing the suture through the suture anchor's bore 135 and then tying a knot 410 at the bottom end of the suture so that the knot seats against face 120 of suture anchor 105. Suture anchor 105 is then attached to the distal end of the installation tool by fitting the suture anchor's barb 115 into the installation tool's slot 635 and pressing the top surface 125 of the suture anchor flush against the installation tool's bottom surface 620. It will be appreciated that in view of the relative dimensioning of the suture anchor and the installation tool, coupling member 110 of the suture anchor is unable to enter the interior of cannula 610, and barb 115 will make a snug fit in cannula slot 635, the fit being snug enough to hold the suture anchor attached to the bottom end of the cannula.

Figure 16:
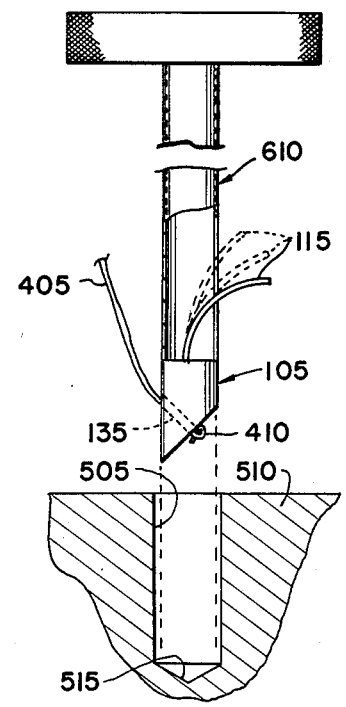
FIG. 16 is a perspective view showing the suture anchor of FIG. 1 being loaded onto the distal end of the suture anchor installation tool of FIGS. 12 and 13.

The suture anchor is then ready to be deployed in a hole 505 formed in a bone 510 (see FIG. 16). It is to be appreciated that the hole formed in the bone is carefully sized according to the dimensions of the suture and suture anchor being deployed in the bone. For example, in the case of a No. 0 suture anchor, the hole formed in bone 510 is sized so as to have a diameter of approximately 0.072 inch and a depth of approximately 0.70 inches.

Figure 17:
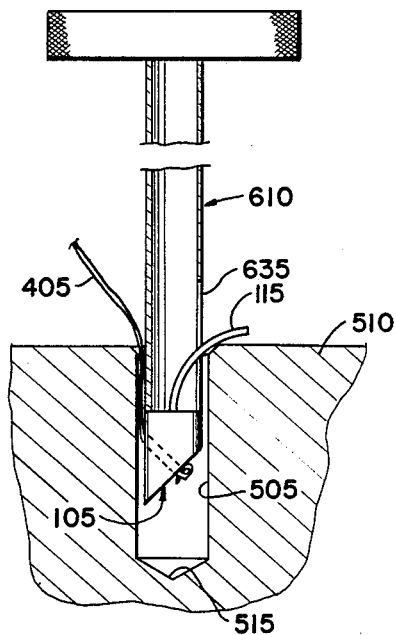
FIG. 17 is a side view in elevation showing the suture anchor of FIG. 1 and the suture anchor installation tool of FIGS. 12 and 13 as the suture anchor is being introduced into a hole formed in bone.
Figure 18:
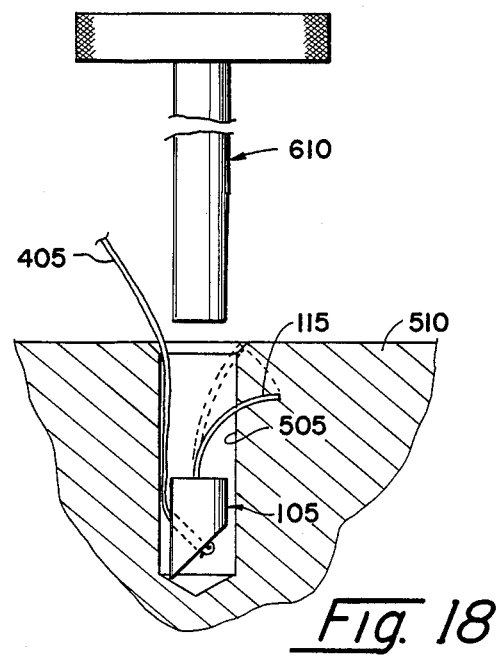
FIG. 18 is a side view in elevation showing the suture anchor of FIG. 1 remaining in the hole formed in the bone as the suture anchor installation tool is withdrawn.

Looking next at FIGS. 17 and 18, the suture anchor is then deployed in the bone hole by pressing the distal end of the cannula down into the predrilled hole 505 in bone 510 until the assembly bottoms out on bone surface 515. As the distal end of the cannula forces the suture anchor down into the bone, the suture anchor's barb 115 engages the side wall of the bone, forcing the barb to retract inwards, into the cannula slot, so that the suture anchor installation tool (and the suture anchor and the suture carried by the suture anchor) can enter bone hole 505. When the bottom of the bone anchor bottoms out in bone hole 505 (see FIG. 18), and the cannula is thereafter withdrawn, the engagement of the suture anchor's barb with the bone wall causes the suture anchor to separate from the cannula, leaving the suture anchor (and its attached suture) securely anchored in the bone.

By using the installation tool 605 just described, a hole only slightly wider than the combined diameters of the cannula 610 and the suture 405 may be drilled in the bone. For example, where a No. 0 suture is to be attached to the bone using a bone anchor 105 and an installation tool 605 of the dimensions indicated above, a hole only approximately 0.072 inch in diameter must be drilled in the bone; where a No. 2 suture is to be attached to the bone using an appropriately sized bone anchor 105 and an appropriately sized installation tool 605, a hole only approximately 0.086 inch in diameter must be drilled in the bone.

A summary table of such sizing is given below:

TABLE 2

| | Suture Size: | |
| --- | --- | --- |
| | No. 0 | No. 2 |
| Suture Anchor Dia. | 0.053 | 0.061 |
| Cannula Diameter | 0.058 | 0.058 |
| Suture Diameter | 0.014 | 0.020 |
| Cannula + Suture Dia. | 0.067 | 0.081 |
| Drill Diameter | 0.072 | 0.086 |
| (Drill hole) − (Suture Anchor) | 0.019 | 0.025 |

Figure 1:
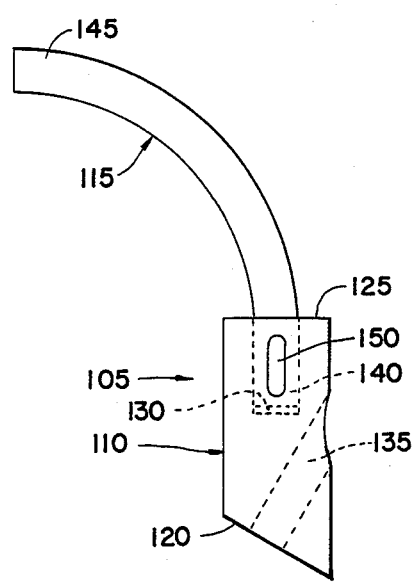
FIG. 1 is a side view in elevation of a prior art suture anchor disclosed in the above-identified U.S. patent application Ser. No. 051,367.
Figure 2:
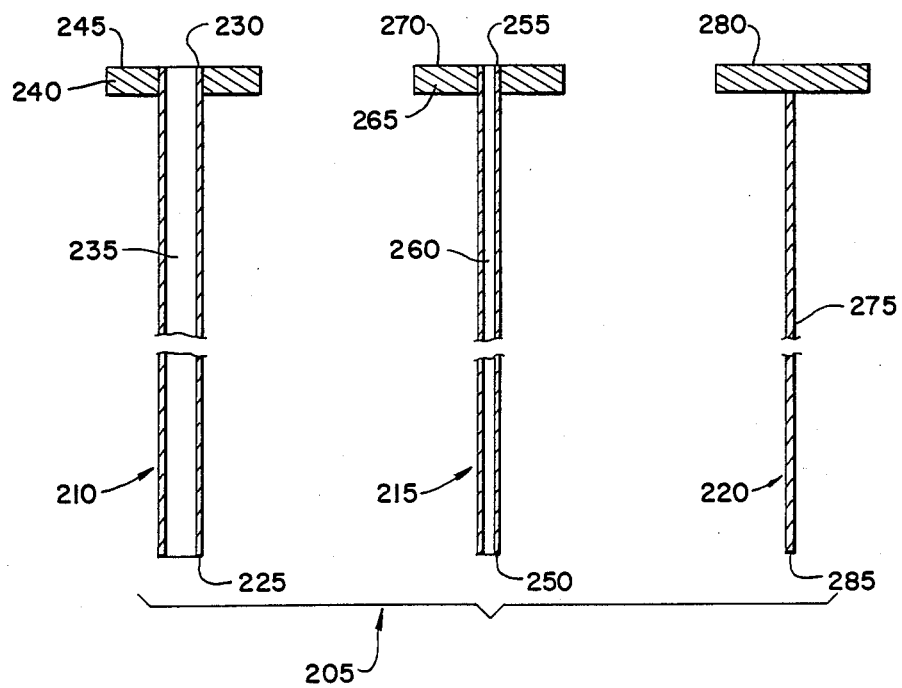
FIG. 2 is a side view in elevation, in section, showing a prior art suture anchor installation tool disclosed in U.S. patent application Ser. No. 051,367.
Figure 3:
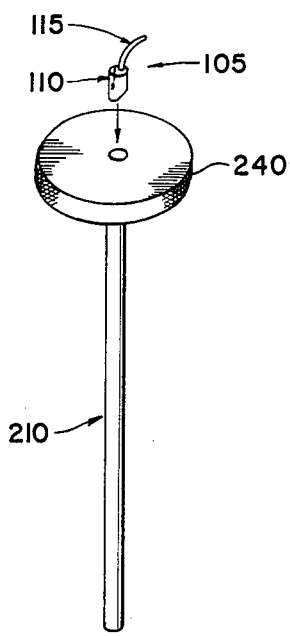
FIGS. 3–11 are a series of views showing the suture anchor of FIG. 1 being deployed into a bone hole using the suture anchor installation tool of FIG. 2.
Figure 4:
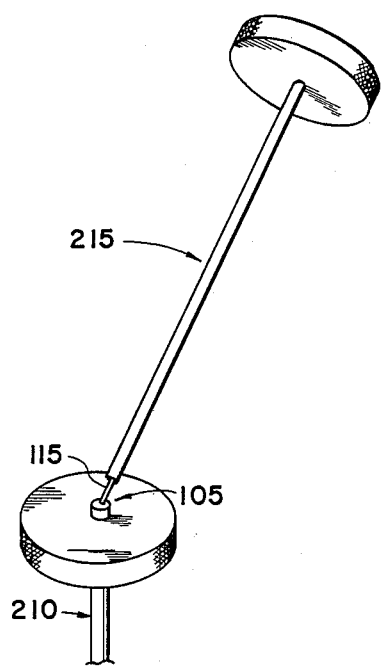
Figure 5:
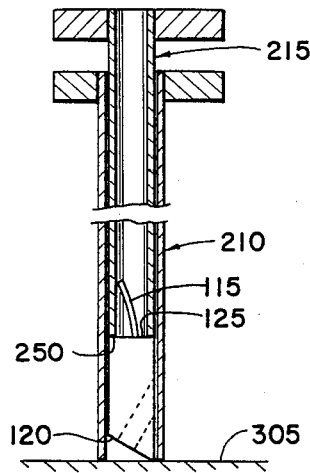
Figure 6:
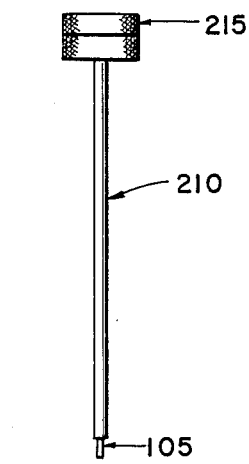
Figure 7:
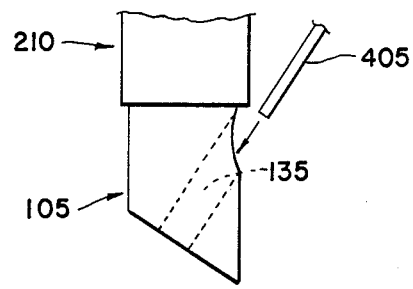
Figure 8:
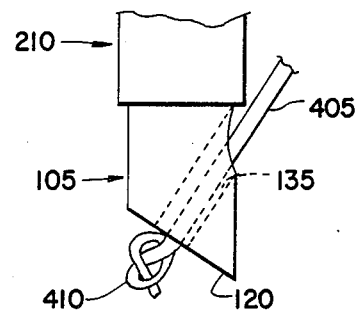
Figure 9:
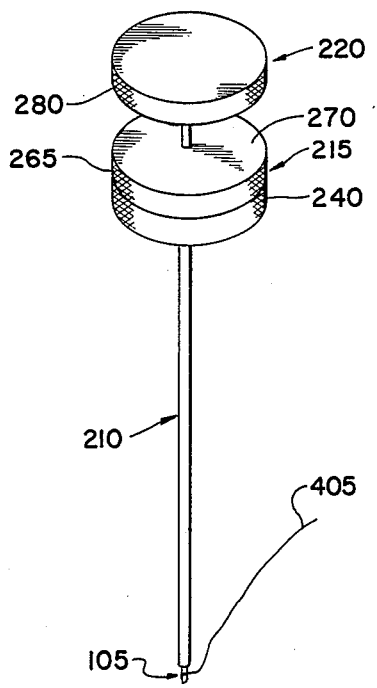
Figure 10:
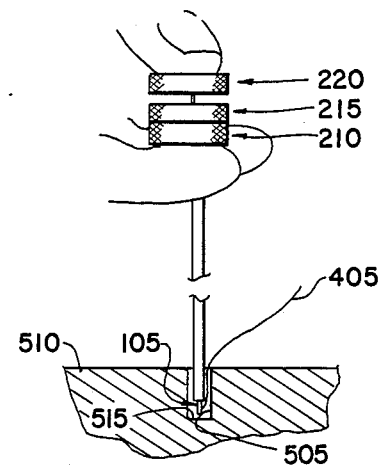
Figure 11:
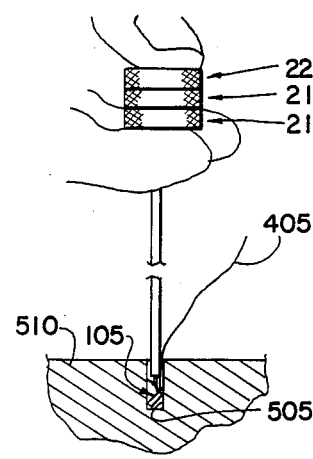

A comparison of Table 2 with Table 1 shows that significantly smaller bone holes may be used when using the installation tool of FIGS. 12 and 13 in place of the three-element installation tool of FIG. 2; as a result, less expansion of barb 115 is required to fix the suture anchor in the bone and a tighter attachment of the suture anchor to the bone results.

It is to be appreciated that certain modifications may be made to the preferred embodiment described above without departing from the scope of the present invention.

Thus, for example, it is anticipated that installation tool 605 could be formed out of a substantially solid rod rather than a hollow cannula; in this case, installation tool 605A (see FIG. 19) would comprise a solid rod 610A having a slot 635A formed therein. Rod 610A would have the same outer diameter as the cannula 610 previously described. It will be appreciated that installation tool 605A functions in exactly the same manner, and provides substantially the same advantages, as the installation tool 605 previously described.

It is also anticipated that some or all of the suture anchor's coupling member 110 could be received within a portion of the installation tool to help hold the suture anchor aligned with the installation tool during insertion of the suture anchor into the bone. Thus, for example, a modified form of installation tool 705 is shown in FIG. 20. Installation tool 705 is identical to the installation tool 605 previously described, except that the cannula 710 is sized to accept a portion of the coupling member 110 of the suture anchor 105. More specifically, cannula 710 has a slightly larger outer diameter than the cannula 610 previously described, and it includes a counterbore 745 which opens on the cannula's distal surface 720 and which terminates in an internal shoulder 750. Shoulder 750 is positioned at a sufficient depth to allow a portion of the suture anchor's coupling member to be received within the cannula's counterbore 745, with the suture anchor's suture-receiving hole still being completely exposed. Preferably counterbore 745 and shoulder 750 are created by relieving a thick-walled hypodermic tubing to the desired depth.

In the case where suture anchor 105 is to be used to anchor a No. 0 suture, so that the suture anchor has the dimension identified above, cannula 710 preferably has an inner diameter of approximately 0.054 inch and an outer diameter of approximately 0.065 inch, slot 735 has a length (i.e., when measured from flat end surface 720 to the slot rear surface 740) of approximately 0.370 inch and a width of 0.031 inch. The cavity which accepts the suture anchor has a length (i.e., when measured from flat end surface 720 to stop 750) of approximately 0.060 inch.

In the case where suture anchor 105 is to be used to anchor a No. 2 suture, so that the suture anchor has the dimension identified above, cannula 710 preferably has an inner diameter of approximately 0.062 inches and an outer diameter of approximately 0.072 inches, slot 735 has a length (i.e., when measured from flat end surface 720 to the slot rear surface 740) of approximately 0.370 inch and a width of approximately 0.031 inch. The cavity which accepts the suture anchor has a length (i.e., when measured from flat end surface 710 to stop 750) of approximately 0.060 inch.

Preferably the suture anchor installation tool 705 has an overall length, when measured from distal end 720 to the rear of its top end, of approximately 4.0 inches.

Looking next at FIG. 21A, there is shown a substantially "solid" installation tool 705A which is adapted to receive a portion of the suture anchor's coupling member in the installation tool's distal end. To this end, installation tool 705A comprises a solid rod 710A having a slot 735A and a blind hole 745A formed therein. During use, the upper end of the suture anchor's coupling member is received in blind hole 745A. Blind hole 745A is sized to have a depth such that the suture anchor's suture-receiving hole will remain exposed when the coupling member is attached to the installation tool. Rod 710A is intended to have the same outer diameter as the cannula 710 previously described.

Looking next at FIG. 21B, there is shown yet another form of the invention. Installation tool 705B is identical to the installation tool 705 previously described, except that the hollow cannula 710B has an internal diameter as large as the diameter of the previously described counterbore 745, in order that the entire suture anchor will be received inside cannula 710A. No counterbore 745 or shoulder 750 is provided; instead, the cannula is crimped inward at 755B at one or more locations to form a stop for engaging the upper surface of the coupling member. Preferably crimps 755B are placed sufficiently far up along cannula 710B so that the entire length of the suture anchor's coupling member may be received within the cannula; in this case, a slot 736B is formed in the cannula, diametrically opposed from the barb-receiving slot 735B, to allow suture 405B to pass through the cannula's side wall. Cannula 710B is intended to have the same outer diameter as the cannula 710 previously described.

The installation tools shown in FIGS. 20, 21A and 21B all have an outer diameter which is greater than the outer diameter of the installation tools shown in FIGS. 12 and 19; nonetheless, smaller bone holes can still be used when using the installation tools of FIGS. 20, 21A and 21B than when using the three-element installation tool of FIG. 2. More specifically, a summary table of the sizing for the tools of FIGS. 20, 21A and 21B is given below:

TABLE 3

|  | Suture Sizes | |
| --- | --- | --- |
|  | No. 0 | No. 2 |
| Suture Anchor (SA) OD | .053 | .061 |
| Inserter OD | .065 | .072 |
| Inserter ID | .054 | .062 |
| Suture Diameter | .014 | .020 |
| (Inserter OD) + (Suture Diameter) | .079 | .092 |
| Drill Diameter | .079 | .094 |
| (Drill Hole) − (SA Diameter) | .026 | .033 |

A comparison of Table 3 and Table 2 with Table 1 shows that significantly smaller bone holes can be used when using the installation tools of FIGS. 12 and 19, or FIGS. 20, 21A and 21B, in place of the three-element installation tool of FIG. 2. In both designs, less expansion of barb 115 is required to fix the suture anchor in the bone.

Furthermore, it is anticipated that installation tools 605, 605A, 705, 705A and/or 705B could be provided with a plurality of slots 635, 635A, 735, 735A and 735B, respectively, for situations where the installation tool is to be used to deploy a suture anchor 105B of the sort having two or more barbs 115B. FIG. 22 illustrates a suture anchor installation tool 605B which may be used to install a suture anchor 105B (having three barbs 115B) in bone.

Yet another modification relates to the method of utilizing the present invention. More specifically, while in all of the foregoing embodiments it was described that the suture is attached to the suture anchor prior to attaching the suture anchor to the installation tool, it is also anticipated that the suture could be attached to the suture anchor after the suture anchor is attached to the installation tool.

Figure 23:
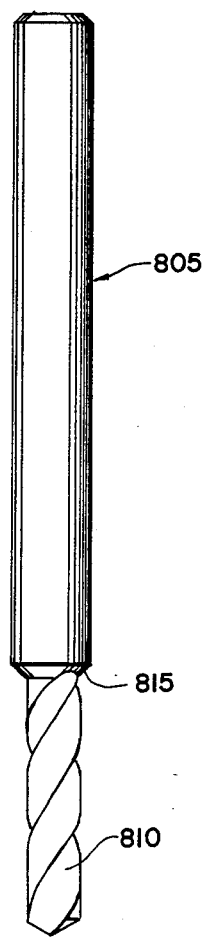
FIG. 23 is a side view in elevation showing a novel drill for forming the hole in the bone which is to receive the suture anchor.
Figure 24:
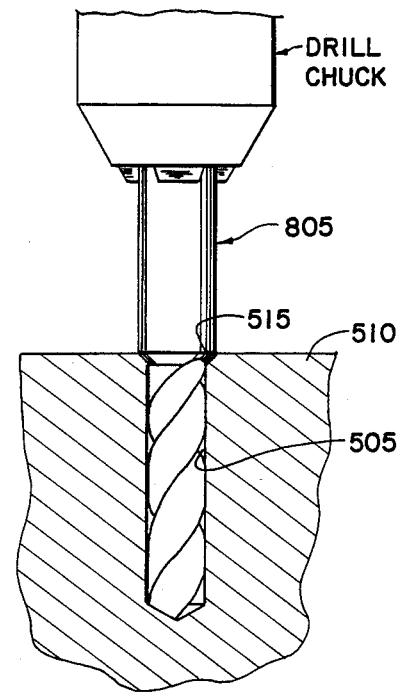
FIG. 24 is a side view in elevation showing the novel drill of FIG. 19 in the process of forming a hole in bone.

Looking next at FIGS. 23 and 24, there is also shown a novel drill 805 for forming the hole 505 in bone 510 which is to receive the suture anchor. Drill 805 comprises a conventional helical drill thread 810 at its distal end. Thread 810 terminates in an inclined frustoconical shoulder 815 which serves as a stop to prevent the drill from penetrating too far into the bone. Shoulder 815 also serves to chamber bone 510 at 515 as shown so as to minimize chafing of the suture about the top of hole 505.

It is also to be appreciated that the suture anchor's coupling member 110 could be formed out of a material other than 6AL4V titanium alloy, and barb 115 could be formed out of a material other than nickel titanium alloy. For example, coupling member 110 could be formed out of titanium and its alloys, ceramics, plastics, stainless steel and other suitable bio-compatible materials, and barb 115 could be formed out of titanium and its alloys, and stainless steel.

Advantages Of The Invention

Numerous advantages are achieved by utilizing the present invention.

First, a novel suture anchor installation tool is disclosed which improves upon the three-element installation tool of the above-identified U.S. patent application Ser. No. 051,367.

Second, a novel suture anchor installation tool is provided which minimizes the gap between the body of the suture anchor and the bone hole, whereby less expansion of the barb will be required to fix the suture anchor in the bone and a tighter attachment of the suture anchor to the bone will result.

Third, a novel suture anchor installation tool is provided in which the suture anchor's barb is not deformed to a straight length when it is loaded in the installation tool, whereby the holding power of the suture anchor will not deteriorate when the suture anchor is stored for a long time in the installation tool prior to use.

And fourth, a novel method for deploying a suture anchor in bone is disclosed.

What is claimed is:

1. A suture anchor installation tool for deploying a suture anchor of the sort comprising (a) a coupling member having an end surface, (b) a barb, said barb having a first end and a second end and being curved in its normal unstressed state and being capable of being elastically deformed to a substantially straight configuration, said barb being attached to said coupling member so that said second end of said barb is substantially displaced from said coupling member when said barb is in its normal unstressed state but is capable of being aligned with said coupling member when said barb is deformed to a substantially straight length, and (c) attachment means for attaching one end of a suture to said suture anchor, said suture anchor installation tool comprising:
an elongated member having an axial bore defined by an inside wall and sized to receive a portion of said coupling member comprising said end surface of said coupling member, a first end and a second end, stop means positioned to engage said end surface for preventing said coupling member from moving along the axis of said elongate member in a first direction, said stop means comprising at least one surface which projects laterally inward from said inside wall of said axial bore, and a slot extending from said first end towards said second end, said slot being sized to accommodate said barb.

2. A suture anchor installation tool according to claim 1 wherein said first end, said counterbore being sized so as to receive a axial bore is a blind bore and said elongated member comprises a reduced diameter bore coupled with and coaxial with said axial bore.

3. A suture anchor installation tool according to claim 2 wherein said at least one surface comprises an annular shoulder at the blind end of said axial bore.

4. A suture anchor installation tool according to claim 1 wherein said elongated member comprises a plurality of slots extending from said first end toward said second end.

5. A suture anchor installation tool according to claim 1 wherein said stop means includes at least one portion of said elongated member which extends radially inwardly into said axial bore so as to reduce the inside diameter of a portion of said axial bore.

6. A suture anchor installation tool according to claim 1 wherein said stop means comprises an integral portion of said elongated member which extends into said axial bore.

7. A suture anchor installation tool according to claim 1 wherein said elongated member is sized to form a friction fit with said suture anchor so as to hold said suture anchor to said installation tool.

8. A suture anchor installation tool according to claim 7 wherein said slot is sized to form a friction fit with said barb so as to hold said suture anchor to said installation tool.

9. A method of anchoring one end of a piece of suture in bone, said method comprising the steps of:
  (1) providing a suture anchor comprising (a) a coupling member, (b) a barb, said barb having a first end and a second end and being curved in its normal unstressed state and being capable of being elastically deformed to a substantially straight configuration, said barb being attached to said coupling member so that said second end of said barb is substantially displaced from said coupling member when said barb is in its normal unstressed state but is capable of being aligned with said coupling member when said barb is deformed to a substantially straight configuration, and (c) attachment means for attaching one end of a suture to said suture anchor;
  (2) attaching said suture anchor to a suture anchor installation tool,
  said suture anchor installation tool comprising an elongated member having a first end and a second end and a slot extending from said first end towards said second end, said slot being sized to accommodate said barb,
  said suture anchor being attached to said elongated member at said first end of said elongated member by fitting said barb into said slot so that said barb extends upward and outward from said first end of said elongated member, through said slot, with said coupling member engaging said first end of said elongated member, and
  attaching said suture to said suture anchor, and
  forming a hole in a bone which is to have said suture attached to it;
  (3) inserting said first end of said installation tool and said suture anchor into said hole in said bone; and
  (4) withdrawing said installation tool from said hole in said bone, leaving said suture anchor disposed in said hole and said suture attached to said bone.

10. A method according to claim 9 wherein said elongated member comprises a hollow portion.

11. A method according to claim 10 wherein said hollow portion has a counterbore at its first end, said counterbore being sized so as to receive a portion of said coupling member.

12. A method according to claim 9 wherein said elongated member comprises a solid rod.

13. A method according to claim 12 wherein said solid rod has a blind hole at its first end, said blind hole being sized so as to receive a portion of said coupling member.

14. A method according to claim 9 wherein said elongated member is sized to form a friction fit with said suture anchor so as to hold said suture anchor to said installation tool.

15. A method according to claim 14 wherein said slot is sized to form a friction fit with said barb so as to hold said suture anchor to said installation tool.

16. A suture anchor installation tool for deploying a suture anchor of the sort comprising (a) a coupling member (b) a barb, said barb having a first end and a second end and being curved in its normal unstressed state and being capable of being elastically deformed to a substantially straight configuration, said barb being attached to said coupling member so that said second end of said barb is substantially displaced from said coupling member when said barb is in its normal unstressed state but is capable of being aligned with said coupling member when said barb is deformed to a substantially straight length, and (c) attachment means for attaching one end of a suture to said suture anchor,
said suture anchor installation tool comprising:
a solid elongated member having a first end and a second end and a slot extending from said first end towards said second end, said slot being sized to accommodate said barb.

17. A suture anchor installation tool according to claim 16 wherein said elongated member comprises a blind hole at its first end, said blind hole being sized so as to receive a portion of said coupling member.

18. A suture anchor installation tool according to claim 16 wherein said elongated member is sized to form a friction fit with said suture anchor so as to hold said suture anchor to said installation tool.

19. A suture anchor installation tool according to claim 18 wherein said slot is sized to form a friction fit with said barb so as to hold said suture anchor to said installation tool.

20. In combination, a suture anchor and a suture installation tool for deploying the suture anchor, said suture anchor comprising (a) a coupling member, (b) a barb, said barb having a first end and a second end and being curved in its normal unstressed state and being capable of being elastically deformed to a substantially straight configuration, said barb being attached to said coupling member so that said second end of said barb is substantially displaced from said coupling member when said barb is in its normal unstressed state but is capable of being aligned with said coupling member when said barb is attachment means for attaching one end of a suture to said suture anchor;
said suture anchor installation tool comprising:
a hollow elongated member having a first end and a second end, said elongated member comprising a counterbore at its first end, said counterbore being sized so as to receive a portion of said coupling member, said elongated member further including a slot being sized to accommodate said barb.

21. Apparatus according to claim 20 wherein said elongated member is sized to form a friction fit with said suture anchor so as to hold suture anchor to said installation tool.

22. Apparatus according to claim 21 wherein said slot is sized to form a friction fit with said barb so as to hold said suture anchor to said installation tool.

23. A method of anchoring a suture anchor in a cavity in a piece of bone, the method comprising the steps of:
(a) providing a suture anchor having (i) a coupling member having an end portion, and (ii) a curved barb attached to said coupling member;
(b) providing a suture anchor installation tool comprising an elongate member having a first end and a second end and a slot extending from said first end toward said second end, said slot being sized to accommodate said barb;
(c) coupling said suture anchor to said suture anchor installation tool so that said tool is in driving engagement with said coupling member and so that said curved barb may be deformed into a substantially straight configuration when the suture anchor is inserted into a cavity in bone;
(d) inserting said first end of said installation tool and said suture anchor into said cavity; and
(e) withdrawing said installation tool from said cavity leaving said suture anchor disposed in said cavity.

24. A method according to claim 23 wherein said elongated member is sized to form a friction fit with said suture anchor so as to hold suture anchor to said installation tool.

25. A method according to claim 24 wherein said slot is sized to form a friction fit with said barb so as to hold said suture anchor to said installation tool.

26. A method of anchoring one end of a piece of suture in bone, the method comprising the steps of:
(1) providing a suture anchor comprising (a) a coupling member, (b) a barb, said barb having a first end and a second end and being curved in its normal unstressed state and being capable of being elastically deformed to a substantially straight configuration, said barb being attached to said coupling member so that said second end of said barb is substantially displaced from said coupling member when said barb is in its normal unstressed state but is capable of being aligned with said coupling member when said barb is deformed to a substantially straight configuration, and (c) attachment means for attaching one end of a suture to said suture anchor;
(2) attaching said suture anchor to a suture anchor installation tool,
said suture anchor installation tool comprising an elongated member having a first end and a second end, a hollow portion open to said first end, and a slot extending from said first end toward said second end, said slot being sized to accommodate said barb,
said suture anchor being attached to said elongated member at said first end of said elongated member by fitting said barb into said slot so that said barb extends upward and outward from said first end of said elongated member, through said slot, and so that said end portion of said coupling member is received in said hollow portion of said elongated member and said elongated member engages said end portion;
(3) attaching said suture to said suture anchor;
(4) forming a hole in a bone which is to have said suture attached to it;
(5) inserting said first end of said installation tool and said suture anchor into said hole in said bone; and
(6) withdrawing said installation tool from said hole in said bone, leaving said suture anchor disposed in said hole and said suture attached to said bone;

wherein steps 2-4 may be performed in any order so long as they are performed after step 1 and before step 5.

27. A method according to claim 26 wherein said elongated member is sized to form a friction fit with said suture anchor so as to hold said suture anchor to said installation tool.

28. A method according to claim 27 wherein said slot is sized to form a friction fit with said barb so as to hold said suture anchor to said installation tool.

* * * * *

UNITED STATES PATENT AND TRADEMARK OFFICE
CERTIFICATE OF CORRECTION

PATENT NO. : 4,899,743

DATED : February 13, 1990

INVENTOR(S) : James E. Nicholson, et al.

It is certified that error appears in the above-identified patent and that said Letters Patent is hereby corrected as shown below:

Claim 2, col. 11, line 62, after the first occurrence of the word "said" (and before the word "axial" in line 63), delete the words -- first end, said counterbore being sized so as to receive a --;

Claim 16, col. 13, line 14, after the word "member" and before the letter "(b)", insert a comma (,);

Claim 20, col. 13, line 42, after the second occurrence of the word "suture", insert the word -- anchor --;

Claim 20, col. 13, line 53, after the word "is" and before the word "attachment", insert the words -- deformed to a substantially straight configuration, and (c) --; and Claim 24, col. 14, line 23, after the word "hold" and before the second occurrence of the word "suture", insert the word -- said --.

Signed and Sealed this

Seventh Day of July, 1992

Attest:

DOUGLAS B. COMER

*Attesting Officer*     *Acting Commissioner of Patents and Trademarks*